US008486686B2

(12) United States Patent
Segueilha et al.

(10) Patent No.: US 8,486,686 B2
(45) Date of Patent: Jul. 16, 2013

(54) LARGE SCALE MICROBIAL CULTURE METHOD

(75) Inventors: Laurent Segueilha, Saint Andre Lez Lille (FR); Ka-Yiu San, Houston, TX (US); George Bennett, Houston, TX (US); Irene Martinez, Houston, TX (US)

(73) Assignee: William Marsh Rice University, Houston, TX (US)

( * ) Notice: Subject to any disclaimer, the term of this patent is extended or adjusted under 35 U.S.C. 154(b) by 220 days.

(21) Appl. No.: 12/747,979

(22) PCT Filed: Dec. 28, 2007

(86) PCT No.: PCT/IB2007/055409
§ 371 (c)(1),
(2), (4) Date: Sep. 2, 2010

(87) PCT Pub. No.: WO2009/083756
PCT Pub. Date: Jul. 9, 2009

(65) Prior Publication Data
US 2010/0317086 A1    Dec. 16, 2010

(51) Int. Cl.
*C12N 1/21*    (2006.01)

(52) U.S. Cl.
USPC ............... 435/252.3; 435/243; 435/252.8

(58) Field of Classification Search
None
See application file for complete search history.

(56) References Cited

U.S. PATENT DOCUMENTS

| | | | |
|---|---|---|---|
| 5,034,105 A * | 7/1991 | Berglund et al. | 204/538 |
| 5,869,301 A | 2/1999 | Nghiem et al. | |
| 7,223,567 B2 * | 5/2007 | Ka-Yiu et al. | 435/71.2 |
| 2003/0175903 A1 | 9/2003 | San et al. | |
| 2005/0042736 A1 | 2/2005 | San et al. | |
| 2006/0040368 A1 | 2/2006 | San et al. | |
| 2006/0046288 A1 | 3/2006 | Ka-Yiu et al. | |
| 2010/0297715 A1 * | 11/2010 | Dehay et al. | 435/145 |

OTHER PUBLICATIONS

Sanchez AM et al: "Novel pathway engineering design of the anaerobic central metabolic pathway in *Escherichia coli* to increase succinate yield and productivity", Metabolic Engineering, Academic Press, May 1, 2005, pp. 229-239, vol. 7, No. 3, Elsevier, XP004879518.

Vemuri GN et al: "Succinate production in dual-phase *Escherichia coli* fermentations depends on the time of transition from aerobic to anaerobic conditions", Journal of Industrial Microbiology and Biotechnology, Jan. 1, 2002, pp. 325-332, vol. 28, Nature Publishing Group, XP003009348.

Becker Sabine et al: "Regulatory 0-2 tensions for the synthesis of fermentation products in *Escherichia coli* and relation to aerobic respiration", Archives of Microbiology, 1997, pp. 290-296, vol. 168, No. 4, Springer-Verlag, XP002501706.

Stokes, JL: "Fermentation of Glucose by Suspensions of *Escherichia Coli*", 1949, pp. 147-158, vol. 57.

International Search Report in Corresponding Application No. PCT/IB2007/055409 Dated Dec. 3, 2008.

* cited by examiner

*Primary Examiner* — Hope Robinson
(74) *Attorney, Agent, or Firm* — Boulware & Valoir

(57) ABSTRACT

A new culture method for producing high levels of a metabolite, such as succinic acid uses oxygen rich culture without pH adjustment to increase the biomass, acclimation in under oxygen lean conditions having <5% partial pressure of oxygen, and the production of high levels of succinate under oxygen deprived conditions. The method can be performed in a single reactor, and is amenable to efficient scale up.

20 Claims, 3 Drawing Sheets

| Agitation | Yield | OD | Vol rate (g/l/h) | Spec rate |
|---|---|---|---|---|
| 300 | 94 | 13,2 | 0,8 | 68 |
| 400 | 103 | 14,7 | 1,1 | 86 |
| 500 | 102 | 14 | 1,0 | 84 |
| 600 | 81 | 14,7 | 0,5 | 45 |

LARGE SCALE MICROBIAL CULTURE METHOD

CROSS-REFERENCE TO RELATED APPLICATIONS

This application is the national phase entry under 35 U.S.C. §371 of International Application No. PCT/IB2007/055409, filed on Dec. 28, 2007, and incorporated by reference herein in its entirety.

BACKGROUND OF THE INVENTION

Anaerobic fermentation and aerobic respiration have been the two metabolic modes of interest for the industrial production of chemicals. Oxygen rich respiration offers very efficient cell growth (growth rate and yield) and converts a high percentage of the carbon source into carbon dioxide and cell mass (see Table 1). Anaerobic fermentation, on the other hand, results in poor cell growth and the synthesis of several fermentation products at high yields (e.g. lactate, formate, ethanol, acetate, succinate, etc.).

TABLE 1

RESPIRATORY VS FERMENTATIVE METABOLISM

| Variable | Anaerobic Fermentation | Anaerobic Respiration | Aerobic Respiration |
| --- | --- | --- | --- |
| Growth Rate | LOW | Intermediate | HIGH |
| Cell Mass | LOW | Intermediate | HIGH |
| Product Yields | HIGH | High/Intermediate | LOW |
| Capital Cost | LOW | LOW | HIGH |
| Energy Input | LOW | LOW | HIGH |

Producing chemicals via oxygen rich processes, however, is more costly than using anaerobic methods for two reasons. First, aerobic fermenters are more expensive to build, due to both the higher cost per unit and the need for smaller fermenters with reduced economy of scale. Secondly, the aerobic fermenters are more costly to operate than their anaerobic counterparts due to low solubility of oxygen, which in turn requires high energy input to ensure appropriate supply of oxygen to the cells. This is especially relevant for the production of commodity chemicals, where fermentation costs can represent 50-90% of the total production cost.

Therefore, anaerobic methods are usually preferred where possible, and it is typical to grow cells to a large number aerobically, and then switch the cells to anaerobic culture for the production of desired molecules. Often, however, the method is unsuccessful, resulting in poor yields and rates.

It has been known for a long time that a mixture of several acids, including succinic acid, is produced starting with the fermentation of *E. coli*, as described by J L Stokes in 1949 in the article entitled "Fermentation of glucose by suspensions of *Escherichia coli*" published in J. Bacteriol., 57: 147-158. However, for each mole of fermented glucose, only 0.3 to 0.4 Moles of succinic acid are produced by the Stokes method.

Thus, to improve the yield, bacteria have been genetically modified so as to inactivate the metabolic pathways that consume the NADH necessary for the production of succinic acid and to activate the metabolic pathways for producing succinate (a salt of succinic acid). In fact, the fermentative metabolic pathway that allows the conversion of oxaloacetate to malate, then fumarate, and finally to succinate requires two moles of NADH per mole of succinate produced. The major metabolic obstacle for the production of succinate is therefore the cellular bioavailability of NADH.

In order to solve this problem, U.S. Pat. No. 7,223,567 describes the use of a recombinant *E. coli* strain which overproduces succinate for the same quantity of available NADH. This *E. coli* strain "SBS550MG-pHL413" has inactivated adhE, ldhA genes (involved in the pathways which consume NADH), inactivated ack-pta genes and the iclR gene (which activate the glyoxylate pathway), and contains a plasmid vector overexpressing an exogenous pyc gene.

The article by Sanchez et al. (entitled "Novel pathway engineering design of the anaerobic central metabolic pathway in *Escherichia coli* to increase succinate yield and productivity" in Metabolic Engineering 7 (2005) 229-239), and U.S. Pat. No. 7,223,567 and US2005042736 have each developed novel culture and production conditions associated with this strain in order to improve its succinic acid production yields. These patents are incorporated by reference in their entirety herein.

In Sanchez et al., U.S. Pat. No. 7,223,567 and US2005042736, SBS550MG-pHL413 is first cultured under aerobic conditions in an Erlenmeyer flask in an LB culture medium in order to produce a maximum amount of biomass, the biomass is concentrated by centrifugation and then transferred under anaerobic conditions into a bioreactor with a rich culture medium to produce succinic acid. In these experiments molar yields of succinate per mole of glucose reached as high as 1.2 or 1.3 in US2005042736, but were generally less than 1.5, but reached as high as 1.7 in U.S. Pat. No. 7,223,567.

However, these experimental culture conditions were developed on a laboratory scale and may be difficult to transpose to an industrial scale, because the first culture step in an Erlenmeyer flask and the centrifugation for recovering the concentrated biomass is not easily adapted for the handling of large volumes. Further, it would be desirable to increase the succinic acid yield and rate of this strain even more, and to make the high succinate yields more reproducible in large scale.

What is needed in the art is a novel culture method that allows high yield and rates of production of compounds, such as succinate, yet is amenable to scale up and is cost effective.

SUMMARY OF THE INVENTION

The present invention generally relates to a new process for culturing microbes to produce high levels of metabolic products, such as succinate, fumarate, malate, lactate, ethanol, glycerol, propanol, butanol and the like, and preferably succinate. The invention also relates to the method of producing such compounds. The invention is exemplified herein with succinate, but can be broadly applied to the culture of microbes to make a variety of end products.

The inventors have discovered that switching directly from aerobic to anaerobic conditions results in very poor molar yield of succinate per mole of glucose—on the order of 0.4-0.8 molar yield. However, when the cells are switched more slowly to anaerobic conditions, by passing through an oxygen lean phase with some, albeit low oxygen, the cells surprisingly produce a much higher molar yield (1.68 in one run) and produce succinate at a higher specific rate (0.116 g/l/hr/OD in one run). Thus, the novel culture methodology improves molar yield to greater than 1.5, preferably to 1.6 and even as high as 1.7, and even more important increases the rate of production. Further increases to 1.8 1.9 or 2 moles of succinate per mole of glucose are possible if the system is further optimized. Thus, the process is much more efficient and reproducible that the prior art methodology, and is amenable to significant scale up.

After much experimentation, a novel culture method that allows high yield and high rate for both cell growth and succinate production in the same bioreactor was developed. The steps involved are: 1) Growth stage under oxygen rich conditions without pH control; 2) An acclimation stage under oxygen lean conditions. This is typically longer than 0.5 hours and may be hours or more. 3) A production phase under oxygen deprived conditions in carbon dioxide rich environment. Carbon may be supplemented as needed during the phases.

The importance of the acclimation stage can be demonstrated by the following experiment where oxygen supply was always plentiful. In this experiment, the cells were grown under a high agitation rate of 800 RPM and switched directly into the anaerobic phase by sparging carbon dioxide into the reactor. The dissolved oxygen in this case was above 60% most of time (data not shown). Without acclimation, the performance of the process suffered. The molar yield was lower than the expected value of ~1.6 and the specific rate was less than 0.06 g/L/h/OD.

| Batch number | Initial agitation (RPM) in oxygen rich phase | Final agitation (RPM) in oxygen rich phase | Air flow rate (L/min) | Base | Molar Yield | Specific Rate (g/L/h/OD) |
|---|---|---|---|---|---|---|
| 30 | 800 | 800 | 2.5 | $NaCO_3$ | ~1.4 | 0.06< |

The results of another run using lower agitation rates, and thus lower oxygen, are shown below. The dissolved oxygen in this case was very low (<5%), yet, the molar yield and the specific production rate were much higher. The molar yield was close to the maximum theoretical yield of 1.6 with high specific production rates of higher than 0.1 g/L/h/OD.

| Batch number | Initial agitation (RPM) in oxygen rich phase | Final agitation (RPM) in oxygen rich phase | Air flow rate (L/min) | Base | Molar Yield | Specific Rate (g/L/h/OD) |
|---|---|---|---|---|---|---|
| 31 | 500 | 500 | 1.5 | $NaCO_3$ | ~1.6 | >0.10 |

By "oxygen rich conditions" what is meant are culture conditions characterized by the presence of oxygen (e.g. aerobic), generally in the form of air. Preferably the partial pressure of oxygen of the fermentation medium is between 60-100%, or 80-90% at t=0, Stirring the culture medium is recommended for the culture of the microbes under oxygen rich conditions, although other means of ensuring adequate oxygenation, such as bubbling and use of oxygen rich head gas, are also available.

By "oxygen lean conditions" what is meant are culture conditions where the oxygen supplied is fully consumed by the microorganism, but the system is not purged of oxygen, thus leading to a partial pressure of oxygen ($pO_2$) in the culture medium <5%, preferably <2%, preferably ≅0-1%. Acclimation or oxygen lean conditions can be achieved by a number of methods. These include changing of the agitation or stirring speed (e.g., lowering to 4-500 rpm), variations in the gas flow rate or the composition of the inlet gas, or by adding more glucose to increase the cell density (and hence higher oxygen demand), or combinations thereof.

Preferably, acclimation is begun once sufficient cell mass has accumulated under oxygen rich conditions, for example until an absorbance at 600 nm greater than around 15, 16, 17, 18, 19 or 20 or greater (i.e. until at least 4 g/l of dry microorganisms) is obtained. Also preferably, the low oxygen acclimation step is carried out after consumption of the most or all of the source of carbon introduced into the culture medium at t=0.

The culture is switched to oxygen deprived conditions when the cells are sufficiently acclimated to low oxygen, and it is possible to test the optimal point as described herein. With the cells, medium, and culture methods used herein, about two hours was sufficient for acclimation, and a pH rise was indicative of acclimation under these conditions.

By "oxygen deprived conditions" what is meant are culture conditions without significant oxygen, e.g., anaerobic. A person skilled in the art will know how to change to oxygen deprived culture conditions. Thus, in a standard fashion the change is possible for example by replacing the oxygen with carbon dioxide generally in the form of carbon dioxide gas or carbonates, or carbon dioxide mixed with other inert gases.

Preferably, oxygen deprived conditions are achieved in a fermentation operation characterized by a permanent injection of $CO_2$ generally in the form of carbon dioxide or carbonates. According to the present invention, for example, $CO_2$ is injected into the bioreactor, at a rate of between 0.1 and 0.5 vvm, preferably 0.3 vvm (volume of $CO_2$ per volume of culture medium and per minute).

By "culture medium" what is meant is a medium comprising the chemical elements necessary for the growth of said microorganism as well as at least one carbon source and one nitrogen source, preferably organic.

The culture medium generally comprises:

A source of potassium and phosphorus ($K_2HPO_4$ for example)
A source of sulphur (($NH_4)_2SO_4$ for example)
A source of magnesium ($MgSO_4$—$7H_2O$ for example)
A source of calcium ($CaCl_2$ for example)
A source of iron (iron sulphate for example)
A source of trace elements (Cu Zn Co Ni B Ti salts for example)
Water
If necessary a pH buffer
One or more sources of carbon, preferably organic (yeast extract, glucose, glycerol, starch, corn by-products, etc.)
One or more sources of nitrogen (yeast extract, corn steep etc.)

Optionally the culture medium according to the invention can also contain an antibiotic (for example ampicillin, carbenicillin or oxacillin, etc.) if the microorganism contains a gene of resistance to said antibiotic, for example on a vector, such as a plasmid, or integrated into the DNA of the organism.

Glucose or starch hydrolysates are mentioned as examples of a carbon source. Preferably according to the invention, the carbon source is glucose, but any carbon source utilizable by the microbe can be used. For example, glycerol, dextrose, corn byproducts, and grains or grasses or their byproducts may all be used to provide a source of carbon.

An example of the composition of the culture medium comprising a carbon source is given hereafter:

| | |
|---|---|
| Glucose | 2 g |
| Tryptone | 20 g |
| Yeast extract | 10 g |
| $(NH_4)HPO_4$ | 3 g |
| $KH_2PO_4$ | 1.2 g |
| $K_2HPO_4$ | 0.7 g |
| $MgSO_4$ | 0.25 g |
| $CaCl_2$ | 0.2 g |
| Thiamine | 0.99 mg |
| Biotin | 1 mg |
| Water | bring volume to 1000 mL |

Preferably, the culture medium is a mineral culture medium. By "mineral culture medium" what is meant is a medium free from proteins, i.e. for which the nitrogen is provided by a mineral pathway, and essentially comprising minerals in solution as well as a carbon source, preferably glucose.

An example of the composition of a mineral culture medium is given hereafter:

| | |
|---|---|
| Glucose | 10 g |
| $(NH_4)HPO_4$ | 6 g |
| $K_2HPO_4$ | 0.5 g |
| $K_2SO_4$ | 1 g |
| KCl | 2 g |
| $MgSO_4 \cdot H_2O$ | 2 g |
| $H_3BO_3$ | 1 mg |
| $MnSO_4$—$7H_2O$ | 20 mg |
| $ZnSO_4$—$7H_2O$ | 4 mg |
| $CuCl_2$—$2H_2O$ | 2 mg |
| $CaCl_2$—$2H_2O$ | 30 mg |
| $FeSO_4$—$7H_2O$ | 60 mg |
| $CoCl_2$—$6H_2O$ | 8 mg |
| $Na_2MO_4\_2H_2O$ | 0.4 mg |
| Biotin | 1 mg |
| Thiamine | 1 mg |
| Distilled water | bring volume to 1000 ml |

By "microorganism capable of producing succinic acid" what is meant is any microorganism that can produce succinic acid, either by its natural metabolism, or as the result of genetic manipulation.

Preferably, the microbes are of the *Escherichia* or *E. coli* species. Particularly preferably according to the invention, the strain of *E. coli* bacterium is a recombinant strain that has been genetically modified in order to produce more succinic acid than the natural strain.

Still, more particularly preferred is a strain which has the genotype ΔadhE ΔldhA ΔiclR Δackpta PYC or ΔadhE ΔldhA ΔiclR Δack PYC or ΔadhE ΔldhA ΔiclR Δpta PYC. This genotype promotes the production of succinic acid by fermentation in the presence of $CO_2$. The symbol Δ indicates that the gene in question has been inactivated, for example by mutation, deletion, interruption, insertion, or "down"-regulation, for example by the introduction of a stop codon, insertion or deletion resulting in a change of reading frame, point mutation, etc.

The genotype ΔadhE ΔldhA ΔiclR Δackpta PYC therefore corresponds to:

| | |
|---|---|
| ΔadhE | inactivation of the alcohol dehydrogenase |
| ΔldhA | inactivation of the lactate dehydrogenase |
| ΔiclR | inactivation of the isocitrate lyase (also known by the name aceA) |
| Δackpta | inactivation of acetate kinase and phosphotransacetylase, can be replaced by a strain where either of acetate kinase or phosphotransacetylase are inactivated (Δack or Δpta) |
| PYC | expression of a pyruvate carboxylase gene. This indicates that the strain expresses the PYC gene, for example by means of a transformation by a plasmid carrying a functional copy of this gene, or by genomic integration of a functional copy of PYC. The PYC gene is advantageously the PYC gene of *Lactococcus lactis*. |

According to a very preferred embodiment, the strain of *E. coli* is the SBS550MG-pHL413 strain. This strain is described in Sanchez et al., Metabolic Engineering, 7 (2005) 229-239, and in U.S. Pat. No. 7,223,567 and US20050042736. Other strains include SBS330MG, SBS330MG, SBS330MG, SBS660MG, and SBS990MG.

Other succinate producing strains that can advantageously be used in the novel method of the invention, include:

| Strain | Genotype |
|---|---|
| SBS110MG | adhE ldhA, $Km^S$ |
| SBS330MG | adhE ldhA iclR, $Km^S$ |
| SBS440MG | adhE, ldhA, iclR, arcA, $Km^S$ |
| SBS550MG | adhE ldhA iclR Δackpta::$Cm^R$, $Km^S$ |
| SBS550-P | adhE ldhA poxB, Δackpta |
| SBS550MG/ptsG | adhE ldhA iclR, ptsG, Δackpta::$Cm^R$, $Km^S$ |
| SBS660MG | adhE, ldhA, iclR, arcA, Δackpta::$Cm^R$, $Km^S$ |
| SBS990MG | adhE ldhA Δackpta::$Cm^R$, $Km^S$ |
| SBS551MG | adhE ldhA iclR, sdhABΔackpta::$Cm^R$, $Km^S$ |
| SBS552MG | adhE ldhA iclR, poxB, sdhABΔackpta::$Cm^R$, $Km^S$ |
| SBS552MG/ptsG | adhE ldhA iclR, ptsG, poxB, sdhABΔackpta::$Cm^R$, $Km^S$ |
| PRP01 | adhE ldhA iclR Δackpta::$Cm^R$, $GalP^+$, $Km^S$ |
| PRP02 | adhE ldhA iclR, ptsHI, Δackpta::$Cm^R$, $Km^S$ |
| SBS1010MGC | adhE, ldhA, fdhNΔackpta::$Cm^R$, $Km^R$ |

Carboxylic acids described herein can be a salt, acid, base, or derivative depending on structure, pH, ions present, and whether esterified. For example, the terms "succinate" and "succinic acid" are used interchangeably herein. Chemicals used herein include formate, glyoxylate, lactate, malate, oxaloacetate (OAA), phosphoenolpyruvate (PEP), and pyruvate. Bacterial metabolic pathways including the Krebs cycle (also called citric acid, tricarboxylic acid, or TCA cycle) can be found in Principles of Biochemistry, by Lehninger as well as other biochemistry texts.

"Reduced activity" is defined herein to be at least a 75% reduction in protein activity, as compared with an appropriate control species. Preferably, at least 80, 85, 90, 95% reduction in activity is attained, and in the most preferred embodiment, the activity is eliminated or "inactivated" (100%). Proteins can be inactivated with inhibitors, by mutation, or by suppression of expression or translation, and the like.

"Overexpression" or "overexpressed" is defined herein to be at least 150% of protein activity as compared with an appropriate control species. Overexpression can be achieved by mutating the protein to produce a more active form or a form that is resistant to inhibition, by removing inhibitors, or adding activators, and the like. Overexpression can also be achieved by removing repressors, adding multiple copies of the gene to the cell, or upregulating the endogenous gene, and the like.

By "culture" what is meant is the culturing of said microorganism for a period until a desired goal is achieved, for example between 0.5 and 72 hours, between 5 and 48 hours, still more preferably between 8 and 24 hours. Preferably the acclimation step is at least two hours, but anywhere from 0.5-5 hours or 1-2 hours.

The optimum culture temperature, is between 20-40° C., preferably around 36-39° C. and even more preferred is 37° C. Different microbes may have different temperature optima, and it is well known how to assess the optimum temperature for microbes.

Preferably, the process according to the invention comprises at least one additional step—that of a second (or more) additions of a source of carbon during the acclimation and/or production stages. Preferably the source and amounts are the same as the initial dose, preferably between 2 and 10 g/L of glucose. However, the source and amounts can also differ.

Preferably the pH of the culture medium before inoculation with said microorganism in is between around 7 and around 8, advantageously around 7.5, and the extra dose of carbon is implemented when the pH has fallen to a value of less than around 7. Afterwards the pH will again rise, to a value greater than around 7, advantageously greater than around 7.2 before the switch to oxygen deprived conditions.

The reduction in the pH to a value of less than around 7 is observed can be linked to the phenomenon of the production of organic acids, then the pH rises again on consumption of part of those organic acids to a value greater than around 7, thus indicating that the cells have successfully acclimated.

By "adjusting the pH" what is meant is the action of maintaining the pH value of the culture medium over a given interval. According to the invention, the pH can be adjusted in different ways. 1) Adjustment over an interval: the pH value is maintained over a certain range of values. The pH value can then vary over time, without however leaving the range considered. 2) "Low point" adjustment: the pH value is maintained above a threshold value. The pH value can then vary over time, without however falling below the threshold value. 3) Adjustment to a single value: the pH value is maintained at this value constantly over time. Advantageously, if the pH is adjusted, it is preferably by the addition of NaOH or $NH_4OH$.

According to another embodiment of the invention, the process according to the invention comprises a step of acidification of the succinate ions present in the culture medium at the end of the production phase for conversion to succinic acid.

Another aspect of the invention relates to a process for obtaining succinic acid characterized in that it comprises a process for the preparation of succinic acid, a step of purification of the succinic acid, and optionally, a step of crystallization of the succinic acid. Advantageously, the purification step comprises bipolar electrodialysis, and the crystallization step is carried out by evapocrystallization and/or crystallization by cooling down in water.

DETAILED DESCRIPTION OF THE INVENTION

The following examples describe preferred embodiments of the process according to this invention, without however limiting the scope.

EXAMPLE 1

PH Control

The detrimental effect of pH control during the oxygen rich cell growth was shown by the following data. Controlling at pH 7.0 with or without salt supplement and at low agitation speed of 500 RPM, the molar succinate yield is always lower than the expected value of ~1.6.

|  | Experiment 1 | Experiment 2 |
|---|---|---|
| Oxygen Rich Medium | LB | LB + salt supplement |
|  | 2 g/L glucose | 2 g/L glucose |
|  | 30 microl/L antifoam 204 | 30 microl/L antifoam 204 |
|  | 200 mg/L Ap | 200 mg/L Ap |
| Conditions | 37 C. | 37 C. |
|  | 500 rpm | 500 rpm |
|  | 1.5 L/min air | 1.5 L/min air |
|  | pH = 7.0 | pH = 7.0 |
| Molar Succinate yield | 1.2≦ | 1.2≦ |

EXAMPLE 2

Succinic Acid Production

This example includes a phase of preculture in an Erlenmeyer flask to generate sufficient inoculant, a phase of culture under oxygen rich conditions in a rich culture medium, i.e. comprising proteins and peptides as a source of nitrogen which can be assimilated by the microorganism. This phase allowing the production of biomass, and is followed by an oxygen lean acclimation phase and then an oxygen deprived production phase, allowing the actual production of succinates. The oxygen rich, lean and deprived phases are carried out in the same fermentor, and the strain used for exemplification herein was SBS550MG-pHL413.

This process is distinguished from the prior art in particular at the end of its oxygen rich phase by the absence of concentration of the biomass by centrifugation and also by the inclusion of an oxygen lean phase.

Preculture Phase:

SBS550MG-pHL413 is precultured in an Erlenmeyer flask for 17 hours at 37° C., under stirring at 125 rpm. 400 ml of medium are inoculated with the strain in a 2-liter Erlenmeyer flask with 2 baffles. The composition of this preculture medium is as follows:

| | |
|---|---|
| tryptone | 10 g/L |
| yeast extract | 5 g/L |
| NaCl | 10 g/L |
| Antibiotic (ampicillin, carbenicillin, oxacillin) | 67 mg/L |

Oxygen Rich and Lean Phases:

The strain, thus precultured, is placed in a 4-litre fermentor in a culture medium the composition of which is as follows:

| | |
|---|---|
| glucose | 2 g/l at T = 0 + 2 g/l after pH rises again |
| tryptone | 20 g/L |
| yeast extract | 10 g/L |
| $K_2HPO_4$ | 0.7 g/L |
| $KH_2PO_4$ | 1.2 g/L |
| $(NH_4)_2SO_4$ | 3 g/L |
| $MgSO_4$ | 0.25 g/L |
| $CaCl_2$ | 0.2 g/L |
| thiamine | 1 mg/L |
| biotin | 1 mg/L |
| ampicillin | 67 mg/L |

The inoculum obtained by preculture in an Erlenmeyer flask represents 3% of the total volume of the medium cultured in the fermentor. The culture conditions during the oxygen rich phase are a temperature of 37° C., stirring at 500 rpm, aeration with air of 2.5 vvm and no adjustment of the pH (the pH was simply adjusted to 7.5 before sterilization of the medium).

Figure 1:
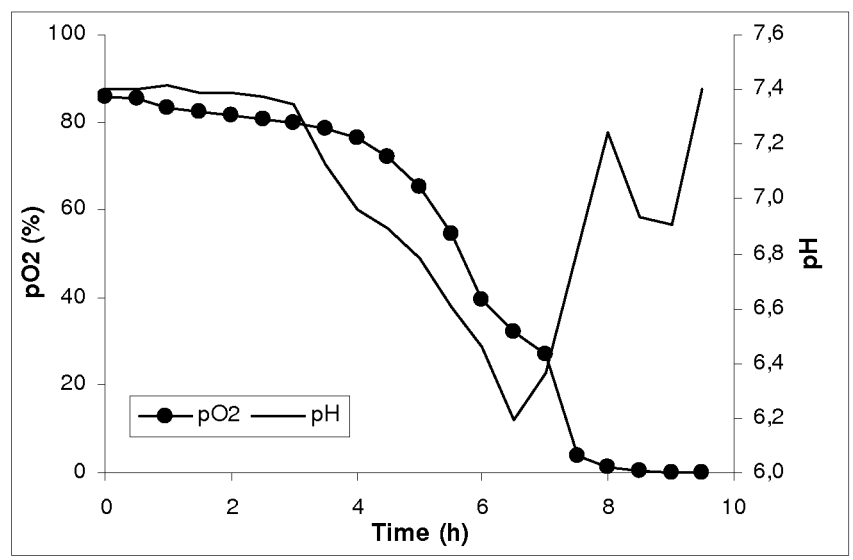
FIG. 1: Curve representing the development during the oxygen rich and oxygen deprived phases of the partial pressure of oxygen ($pO_2$) (left-hand scale) and of the pH (right-hand scale) according to the conditions of Example 2.

A curve representing the partial pressure of oxygen ($pO_2$) (left-hand scale) and of the pH (right-hand scale) is shown in FIG. 1. During the first pH peak at 7.2 observed at the end of 8 hours, 2 g/l of glucose are added (indicated in the composition of the culture medium as "+2 g/l after pH rises again"). After this addition of glucose, a reduction in the pH is observed to below 7 then a second pH peak at 7.4 after 9.5 hours.

It is noted that as a result of the growth of the microorganism, from 7 and a half hours, the partial pressure of oxygen ($pO_2$) falls to <1% (oxygen lean conditions) and remains thus for 2 hours. This reflects, at the end of culture, and for 2 hours, almost complete consumption by the microorganism of the oxygen supplied to the culture medium. This phase of growth is called the "oxygen lean phase" herein.

Oxygen Deprived Phase:

Next the strain is placed under oxygen deprived conditions by replacing the supply of oxygen with an injection of $CO_2$ at 0.3 vvm, at 37° C., the stirring being carried out at 250 rpm. The pH of the culture medium is adjusted to pH 7 by a 10M solution of 5M NaOH.

The following compounds are added to the culture medium:

| | |
|---|---|
| Glucose | 20 g/L |
| IPTG (inducer) (if needed) | 0.238 g/L |

The final results are as follows:

| Duration in hours | Absorbance in OD at 600 nm | glucose in g/L | succinic acid in g/L |
|---|---|---|---|
| Oxygen Rich phase | | | |
| 7.7 | 11.5 | 0.0 | 0.0 |
| Oxygen Lean Phase | | | |
| 9.5 | 16.7 | 0.0 | 0.0 |
| Oxygen Deprived Phase: t = 9.5 h (under CO2) | | | |
| 23.5 | 14 | 6 | 12.2 |
| 29.5 | 14 | 3.1 | 15.4 |
| At t = 29.5 h: Addition of glucose at 15 g/L | | | |
| 48 | 12 | 11.6 | 21 |
| 72 | 10.6 | 4.3 | 27.1 |

It is therefore observed that the implementation of the process according to the invention allows a significant production of succinic acid in the final phase.

EXAMPLE 3

Effect of Oxygen During Growth

Figure 2:
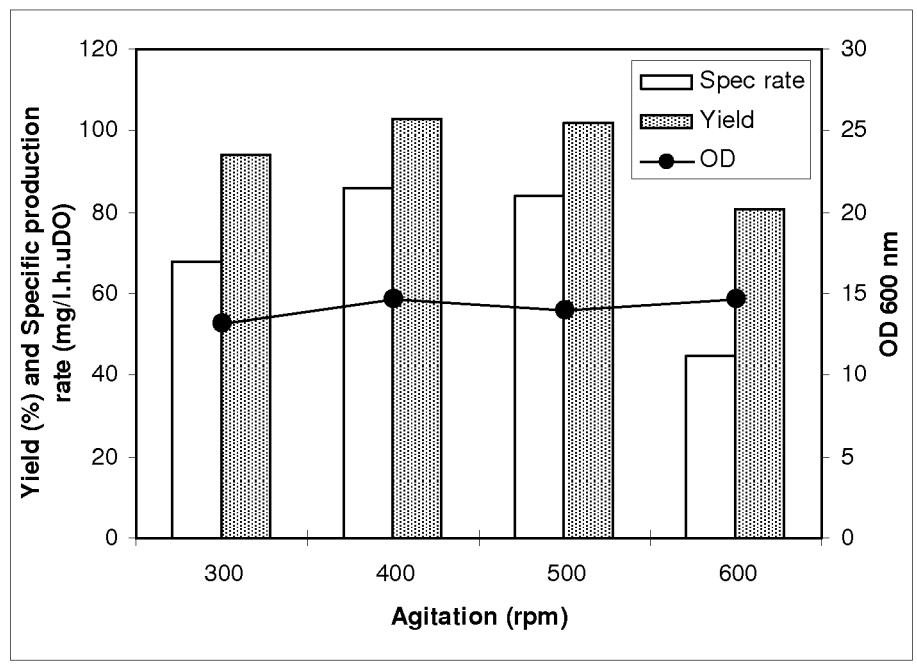
FIG. 2: Effect of stirring in the oxygen rich phase on the performance of the biomass in production (measured after culture for 18 hours under $CO_2$) according to the conditions of Example 3.

This example aims to study the effect of oxygen via variations in stirring rate. The production of succinic acid by the SBS550MG-pHL413 strain is carried out under $CO_2$ in the absence of growth. The growth phase is carried out beforehand under oxygen rich conditions according to the "oxygen rich phase" protocol of Example 2, and the effect of stirring at 18 hours under $CO_2$ is shown in FIG. 2.

A very significant effect of this parameter on the performance is observed. The optimum is situated at 400-500 rpm for productivity and yield, both of which are greatly reduced at 600 rpm.

The transfer of oxygen therefore constitutes an important parameter for the induction of the metabolic pathways involved in the production of succinic acid. One hypothesis would be that the induction requires a phase with little or no dissolved oxygen content (pO2) at the end of the oxygen rich phase to acclimate the cells to low oxygen—In other words, an oxygen lean phase with very low oxygen, before the system is purged of oxygen under the oxygen deprived phase.

EXAMPLE 4

Effect of pH Adjustment

This example includes a preculture phase, a phase of culture under oxygen rich conditions in a rich culture medium (as opposed to mineral), an oxygen lean phase and an oxygen deprived phase allowing the actual production of succinic acid by fermentation. The phases are carried out in the same fermentor, and the strain used for exemplification is the SBS550MG-pHL413 strain.

This example differs from above mainly in that the pH is adjusted during the oxygen rich phase and the oxygen deprived phase to 6.75 low point.

Pre-Culture Phase:
See Example 2.

Oxygen Rich and Oxygen Lean Phases:
The strain precultured in this way is placed in a 15 L fermentor in the culture medium of Example 2. The inoculum obtained by preculture in an Erlenmeyer flask represents 3% of the total volume of the medium cultured in the fermentor. The culture conditions during the oxygen rich phase are a temperature of 37° C., stirring at 400 rpm, aeration of 1 vvm adjustment to 6.75 low point with a 5N solution of NaOH. The partial pressure of oxygen is <1% for two hours (oxygen lean phase).

Figure 3:
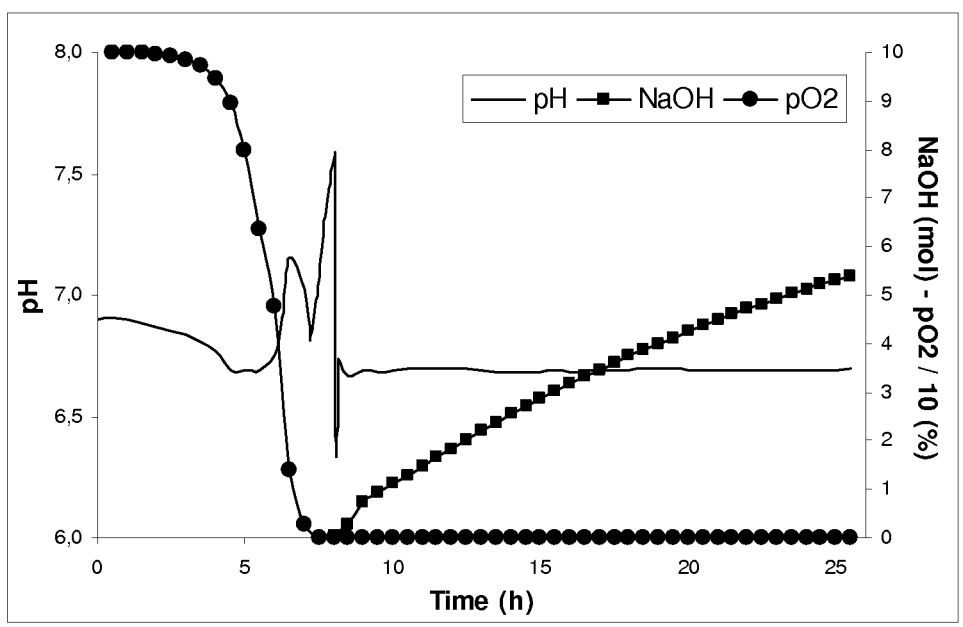
FIG. 3: Curve representing the development during the oxygen rich phase and the oxygen deprived phase, of the partial pressure of oxygen ($pO_2$), of the pH and of the quantity of NaOH added to the culture medium according to the conditions of Example 4.

The curves representing the development of the partial pressure of oxygen ($pO_2$) (left-hand scale) and of the pH (right-hand scale) and NaOH used to balance the pH is shown in FIG. 3. During the first pH peak at 7.2 observed at the end of 7 hours, 2 g/l of glucose are added (indicated in the composition of the culture medium as "+2 g/l after pH rises again"). After this addition of glucose, a reduction in the pH is observed to below 7 then a second pH peak at 7.6 at the end of 8 hours. Concomitantly, as from 7 hours the partial pressure of oxygen ($pO_2$) falls to <2% (oxygen lean conditions). The culture is then changed to an oxygen deprived phase after culture for 8 hours.

Oxygen Deprived Phase:

Next the strain is placed under oxygen deprived conditions by replacement of the oxygen supply with an injection of $CO_2$ at 0.2 vvm, at 37° C., the stirring being carried out at 250 rpm. The pH of the culture medium is adjusted to pH 6.75 low point with a 5N solution of NaOH. Glucose is added at 20 g/L to the culture medium under oxygen deprived conditions:

The results are as follows:

| Duration (hours) | Absorbance OD at 600 nm | Glucose in g/L | Succinic acid in g/L |
|---|---|---|---|
| Oxygen Rich Phase | | | |
| 7 | 8.5 | 0.0 | 0.0 |
| Oxygen Lean Phase | | | |
| 8 | 15.4 | 0.0 | 0.0 |
| Oxygen Deprived Phase (under $CO_2$) | | | |
| 26 | 10 | 0 | 20 |

EXAMPLE 5

Mineral Medium

The tables below shows the two media developed by this work. The medium MIN-N is defined to be used with pH adjustment with ammonium hydroxide.

| | MIN | MIN-N |
|---|---|---|
| $K_2HPO_4$ | 0.5 | 2.8 |
| $K_2SO_4$ | 1.0 | 1.0 |
| KCl | 2.0 | |
| $(NH_4)_2HPO_4$ | 6.0 | 0.4 |
| $MgSO_4, 7H_2O$ | 2.0 | 2.0 |
| Adjustment of the pH | NaOH | $NH_3$ |

The media presented above make it possible, complemented with 20 g/l of glucose, to obtain a sufficient biomass (absorbance 600 nm >15) to carry out a significant (>15 g/l) succinic production over 18 hour of oxygen deprived phase under $CO_2$.

EXAMPLE 6

Mineral Medium with pH Adjustment

Another process for obtaining succinic acid comprises uses the mineral medium developed above and includes preculture phase, a phase of subculture in the fermentor, a phase of culture under oxygen rich conditions in a mineral culture medium allowing the production of biomass, an oxygen lean phase and an oxygen deprived phase allowing the actual production of succinic acid by fermentation. The phases are carried out in the same fermentor and the strain used for exemplification is SBS550MG-pHL413.

Preculture Phase:

The SBS550MG-pHL413 strain is pre-cultured in an Erlenmeyer flask for less than 24 hours at 37° C., accompanied by gentle stirring at 125 rpm. 500 ml of pre-culture medium are inoculated from a frozen tube of inoculum into a 2-litre Erlenmeyer flask.

The composition of this pre-culture medium is as follows:

| | |
|---|---|
| Tryptone | 10 g/l |
| Yeast extract | 5 g/l |
| NaCl | 10 g/l |
| $KH_2PO_4$ | 3 g/l |
| $Na_2HPO_4$ | 6 g/l |
| $NH_4Cl$ | 1 g/l |
| $MgSO_4, 7H_2O$ | 0.25 g/l |
| NaCl | 0.5 g/l |
| Antibiotic (ampicillin, carbenicillin, oxacillin) | 67 mg/L |

Subculture Phase:

The composition of this subculture medium is as follows:

| | |
|---|---|
| Glucose | 10 g/l |
| $(NH_4)_2HPO_4$ | 6 g/l |
| $K_2HPO_4$ | 0.5 g/l |
| $K_2SO_4$ | 1 g/l |
| KCl | 2 g/l |
| $MgSO_4, 7H_2O$ | 2 g/l |
| $FeSO4 \cdot 7H2O$ | 60 mg/l |
| $CaCl2 \cdot 2H2O$ | 30 mg/l |
| $ZnSO_4 \cdot 7H_2O$ | 4 mg/l |
| $CuCl_2 \cdot 2H_2O$ | 2 mg/l |
| $MnSO_4 \cdot H_2O$ | 20 mg/l |
| $CoCl_2 \cdot 6H_2O$ | 8 mg/l |
| $H_3BO_3$ | 1 mg/l |
| $Na_2MoO_4 \cdot 2H_2O$ | 0.4 mg/l |
| Biotin | 1 mg/l |
| Thiamine | 1 mg/l |
| Ampicillin | 67 mg/l |

The inoculum obtained by preculture in an Erlenmeyer flask represents 6% of the total volume of the medium cultured in the fermentor. The subculturing is carried out over more than 20 hours in a fermentor at a temperature of 37° C. accompanied by stirring at 450 rpm with a partial pressure of oxygen greater than 0% and aeration of 1 vvm. The pH of the culture medium is adjusted to 6.75 low point with a 5 N soda solution.

Oxygen Rich and Lean Phases:

After this subculture phase, the strain is placed in a 20 L fermentor in a culture medium the composition of which is as follows:

| | |
|---|---|
| Glucose: 10 g/l at the start + 10 g/l after consumption | |
| $(NH_4)_2HPO_4$ | 6 g/l |
| $K_2HPO_4$ | 0.5 g/l |
| $K_2SO_4$ | 1 g/l |
| KCl | 2 g/l |
| $MgSO_4, 7H_2O$ | 2 g/l |
| $FeSO_4 \cdot 7H_2O$ | 60 mg/l |
| $CaCl_2 \cdot 2H_2O$ | 30 mg/l |

-continued

| Glucose: 10 g/l at the start + 10 g/l after consumption | |
|---|---|
| $ZnSO_4 \cdot 7H_2O$ | 4 mg/l |
| $CuCl_2 \cdot 2H_2O$ | 2 mg/l |
| $MnSO_4 \cdot H_2O$ | 20 mg/l |
| $CoCl_2 \cdot 6H_2O$ | 8 mg/l |
| $H_3BO_3$ | 1 mg/l |
| $Na_2MoO_4 \cdot 2H_2O$ | 0.4 mg/l |
| Biotin | 1 mg/l |
| Thiamine | 1 mg/l |
| Ampicillin | 67 mg/l |

The inoculum obtained by preculture in an Erlenmeyer flask represents 13% of the total volume of the medium cultured in the fermentor. The aeration is maintained at 1 vvm, the temperature at 37° C. and the pH of the culture medium is adjusted to 6.75 low point with a 5 N soda solution. Firstly, the partial pressure of oxygen is maintained above 20% by stirring the culture medium at 450 rpm.

When the 10 g/l of glucose have been consumed by the strain, the stirring is reduced to 400 rpm in order to change to oxygen lean conditions (with a partial pressure of oxygen <1%).

Oxygen Deprived Phase:

After the oxygen rich and lean phases, the strain is placed under oxygen deprived conditions by replacing the supply of oxygen by injection of $CO_2$ at 0.2 vvm, at 37° C., the stirring being at 250 rpm. The pH of the culture medium is adjusted to pH 6.75 with a 5N NaOH solution. Glucose is added at 20 g/l to the culture medium under oxygen deprived conditions.

The table below summarizes the results after 18 h of production:

| BASE Oxygen rich phase | Medium Oxygen rich phase | Oxygen lean phase | pH rise Oxygen rich phase | Specific growth rate (=μ) $h^{-1}$ Aerobic phase | OD 600 nm Oxygen rich phase | Succinate Yield (% g/g) $CO_2$ phase | Specific Succinate rate (g/h/OD) $CO_2$ phase |
|---|---|---|---|---|---|---|---|
| NaOH | MIN | YES | With | 0.31 | 16.6 | 92 | 0.06 |

A new protocol was used to verify the influence on the production of three important factors of the oxygen rich phase:

Base used ($NaOH/NH_3$).

Presence of an oxygen lean phase (low oxygen content) at the end of the oxygen rich phase.

Rise of pH again at the end of the oxygen lean phase (consumption of the acids produced).

The table below summarizes the results obtained with each of the combinations of these factors (after 18 hours of production)—the results obtained with the basic protocol presented above are shown in the third line of this table.

| BASE Oxygen rich phase | Medium Oxygen rich phase | Oxygen lean phase | pH rise in oxygen rich phase | Specific growth rate (=μ) $h^{-1}$ Aerobic phase | Abs 600 nm Oxygen rich phase | Succinate Yield (% g/g) $CO_2$ phase | Specific Succinate rate (g/h/OD) $CO_2$ phase |
|---|---|---|---|---|---|---|---|
| NaOH | MIN | NO | Without | 0.33 | 18.0 | — | <0.01 |
| NaOH | MIN | YES | Without | 0.30 | 16.1 | 85 | 0.03 |
|  | MIN | YES | With | 0.31 | 16.6 | 92 | 0.06 |
| NH3 | MIN N | NO | Without | 0.39 | 22.3 | — | <0.01 |
| NH3 | MIN N | YES | Without | 0.33 | 17.9 | 68 | 0.05 |
| NH3 | MIN N | YES | With | 0.34 | 17.2 | 71 | 0.05 |

This demonstrates that the oxygen lean phase is needed to obtain significant specific productivity of the biomass (>0.01 g/h/OD). The final pH rise during aerobic phase gives also a positive effect on both yield and specific rate (the yield in succinic acid is calculated on the glucose consumed during the production phase and expressed in g/g×100).

Overall, the effects observed are similar to those obtained with the rich media, which validates the protocol.

Effect of the Oxygen Lean Phase:

These tests confirm the pre-eminence of this factor. This phase is absolutely indispensable for inducing the production of succinic acid. Without an oxygen lean phase (see bold lines), the succinate yield drops to negligible.

Effect of $NH_3$/Na and pH Management:

The addition of a rise in the pH again at the end of the oxygen rich phase on a soda-based medium allows a clear improvement in the activity of the biomass and the yield (92%).

The use of ammonium hydroxide induces an improvement in the growth and the specific consumption speed of the glucose in the production phase.

EXAMPLE 7

Corn Based Medium without pH Adjustment

This Example includes a preculture phase, a phase of culture under oxygen rich conditions in a culture medium comprising corn steep as nitrogen source and glucose as carbon source, this phase allowing the production of biomass, an oxygen lean phase and an oxygen deprived phase allowing the actual production of succinic acid. The strain used for exemplification is the SBS550MG-pHL413 strain.

Preculture Phase:

See Example 2.

Oxygen Rich and Lean Phases:

After preculture, the strain is placed in a 4 L fermentor stirred at 400 rpm in a culture medium the composition of which is as follows:

| Glucose: 2 g/l at the start + 2 g/l after rise of the pH | |
|---|---|
| Corn steep: 60 g/l | |
| $(NH_4)_2SO_4$ | 0.25 g/l |
| $K_2HPO_4$ | 0.7 g/l |
| $KH_2PO_4$ | 1.2 g/l |
| KCl | 2 g/l |
| $CaCl_2$ | 0.2 g/l |
| $MgSO_4$ | 0.25 g/l |
| ampicillin | 0.067 g/l |
| biotin | 0.001 g/l |
| thiamine | 0.001 g/l |

Oxygen Deprived Phase:

Next the strain is placed under oxygen deprived conditions by replacing the oxygen supply by injection of $CO_2$ at 0.3 vvm, at 37° C., the stirring being at 250 rpm. The pH of the culture medium is adjusted to pH 6.4 by a solution of 5N NaOH. Glucose is added at 20 g/L to the culture medium under oxygen deprived conditions. 15 g/l of glucose are added after 24 h of culture under oxygen deprived conditions and 4 g/l after 48 h.

The results obtained are as follows:

| Cumulative duration in h | Absorbance in OD at 600 nm | glucose in g/L | succinic in g/L |
|---|---|---|---|
| Oxygen Rich Phase | | | |
| 0 | 6 | 2.0 | 0.0 |
| 6.8 | 22 | / | / |
| 7.5 | 27 | / | / |
| Oxygen Lean Phase | | | |
| 9 | 33.5 | 0.0 | 0.0 |
| Oxygen Deprived Phase (under CO2 after 9 h) | | | |
| 24 | 20.0 | 0.6 | 15.5 |
| addition of 15 g/L glucose | | | |
| 48 | 14.5 | 2.4 | 26.8 |
| addition of 4 g/L glucose after 48 h | | | |
| 50 | 16.5 | 5.8 | 26.9 |
| 54.5 | / | 4.2 | 28 |
| 72 | 13.5 | 0 | 32.3 |

Overall yield on glucose: 88%

The invention claimed is:

1. A method of culturing microbes in a single reactor to produce a metabolite, comprising the following steps:
   a) inoculating a culture medium containing a carbon source in a reactor with a microbe that has the ability to produce a metabolite,
   b) cultivating said microbe under oxygen rich conditions in said reactor,
   c) acclimating said microbe to oxygen lean conditions of less than 5% oxygen in said reactor,
   d) changing to oxygen deprived conditions in said reactor by purging with $CO_2$ or $CO_2$ mixed with an inert gas, and
   e) culturing said microbe under said oxygen deprived conditions in said reactor for a period of time sufficient to produce said metabolite.

2. The method of claim 1, wherein said metabolite is selected from the group consisting of succinic acid, malic acid, fumaric acid, lactic acid, glycerol, ethanol, isopropanol, and butanol.

3. The method of claim 1, wherein said microbe is *Escherichia coli*.

4. The method of claim 1, wherein said microbe contains an inactivation of the adhE, ldhA, ack-pta and/or iclR genes and has an overexpressed pyc gene.

5. The method of claim 1, wherein the microbe has the genotype ΔadhE ΔldhA ΔiclR Δackpta PYC or ΔadhE ΔldhA ΔiclR Δack PYC or ΔadhE ΔldhA ΔiclR Δpta PYC.

6. The method of claim 1, wherein the microbe is SBS550MGpHL413.

7. The method of claim 4, wherein the culture medium is a mineral culture medium.

8. The method of claim 7, wherein it comprises at least one addition of extra carbon during step c) or step e).

9. The method of claim 8, wherein extra carbon is added when the pH of the culture medium has fallen to a value of less than around during said acclimating step.

10. The method of claim 9, wherein step d) is implemented when the pH of the culture medium has risen to about 7.2.

11. The method of claim 9, wherein step d) is implemented when said culture medium has been under oxygen lean conditions for at least two hours.

12. The method of claim 1, wherein step c) is initiated when most of the carbon source in the culture medium is consumed.

13. The method of claim 1, wherein said acclimating step begins when said microbe produces an absorbance at 600 nm of greater than 15.

14. The method of claim 1, characterized in that steps a) to e) are carried out in a fermentor.

15. The method of claim 1, characterized in that it also comprises a step f) of acidification of the succinate ions present in the culture medium at the end of step e) for their conversion to succinic acid.

16. The method of claim 1, wherein said metabolite is succinic acid.

17. A method of culturing microbes in a single reactor to produce a metabolite, comprising the following steps:
   a) inoculating a culture medium in a reactor with a microbe that has the ability to produce a metabolite,
   b) cultivating said microbe under oxygen rich conditions without pH control in said reactor until reaching an $OD_{600}$ of at least 15;
   c) acclimating said microbe to oxygen lean conditions less than 5% oxygen in said reactor for >0.5 hour;
   d) changing to oxygen deprived conditions in said reactor when said culture medium pH rises;
   e) culturing said microbe under said oxygen deprived conditions in said reactor for a period of time sufficient to produce said metabolite; and
   f) isolating said metabolite.

18. The method of claim 17, wherein said metabolite is succinic acid.

19. The method of claim 17, wherein said metabolite is succinic acid and a molar yield of said succinate is >1.5.

20. The method of claim 17, wherein said metabolite is succinate and said microbe has a genotype selected from the group consisting of
   ΔadhE, ΔldhA, ΔiclR, Δackpta, and PYC;
   ΔadhE, ΔldhA, ΔiclR, Δack, and PYC;
   ΔadhE, ΔldhA, ΔiclR, Δpta, and PYC;
   ΔadhE and ΔldhA;
   ΔadhE, ΔldhA, and Δiclr;
   ΔadhE, ΔldhA, ΔiclR, and ΔarcA;
   ΔadhE, ΔldhA, ΔiclR, and Δackpta;
   ΔadhE, ΔldhA, ΔiclR, Δpoxb, and Δackpta;
   ΔadhE, ΔldhA, ΔiclR, ΔptsG, and Δackpta;
   ΔadhE, ΔldhA, ΔiclR, ΔarcA, and Δackpta;
   ΔadhE, ΔldhA, and Δackpta;
   ΔadhE, ΔldhA, ΔiclR, ΔsdhA, and Δackpta;

ΔadhE, ΔldhA, ΔiclR, ΔpoxB, ΔsdhAB and Δackpta;
ΔadhE, ΔldhA, ΔiclR, ΔptsG, ΔpoxB, ΔsdhAB, and Δackpta;
ΔadhE, ΔldhA, ΔiclR, ΔptsHI, and Δackpta; and
ΔadhE, ΔldhA, ΔfdhN, and Δackpta.

* * * * *

UNITED STATES PATENT AND TRADEMARK OFFICE
CERTIFICATE OF CORRECTION

| | | |
|---|---|---|
| PATENT NO. | : 8,486,686 B2 | Page 1 of 1 |
| APPLICATION NO. | : 12/747979 | |
| DATED | : July 16, 2013 | |
| INVENTOR(S) | : Segueilha et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 318 days.

Signed and Sealed this
Twelfth Day of May, 2015

Michelle K. Lee
*Director of the United States Patent and Trademark Office*